United States Patent
Yamaguchi et al.

[11] Patent Number: 5,943,134
[45] Date of Patent: Aug. 24, 1999

[54] METHOD OF MEASURING THICKNESS AND REFRACTIVE INDICES OF COMPONENT LAYERS OF LAMINATED STRUCTURE AND MEASURING APPARATUS FOR CARRYING OUT THE SAME

[75] Inventors: Ichirou Yamaguchi, Wako; Takashi Fukano, Nerima-ku, both of Japan

[73] Assignee: The Institute of Physical and Chemical Research, Wako, Japan

[21] Appl. No.: 08/877,502

[22] Filed: Jun. 17, 1997

[30] Foreign Application Priority Data

Jun. 17, 1996 [JP] Japan .................................. 8-155828

[51] Int. Cl.$^6$ .............................................. G01B 9/02
[52] U.S. Cl. ................................... 356/357; 356/359
[58] Field of Search ..................................... 356/357, 359

[56] References Cited

U.S. PATENT DOCUMENTS 5,465,147  11/1995  Swanson ................................. 356/345

*Primary Examiner*—Robert Kim
*Attorney, Agent, or Firm*—Jacobson, Price, Holman & Stern, PLLC

[57] ABSTRACT

A light beam emitted by a light source is projected through a collimator lens, a beam splitter and an objective on a sample having a laminated structure. The light beam reflected from the sample travels through the beam splitter to a detector and the detector provides a confocal signal. The detector provides an interference signal upon the reception of the reflected light beam and a reference light beam reflected by a reference mirror. The sample and the reference mirror are moved on the basis of the confocal signal and the interference signal, and the thickness and the refractive index of layer of the sample are determined on the basis of the respective displacements of the sample and the reference mirror.

6 Claims, 7 Drawing Sheets

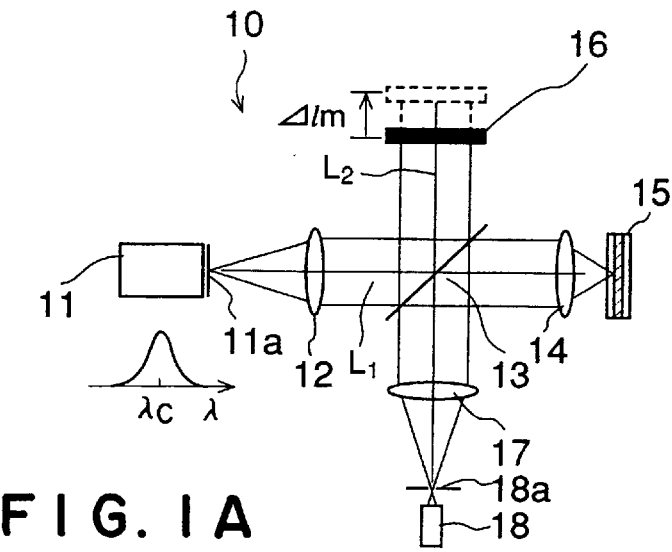
F I G. I A
F I G. I B  F I G. I C
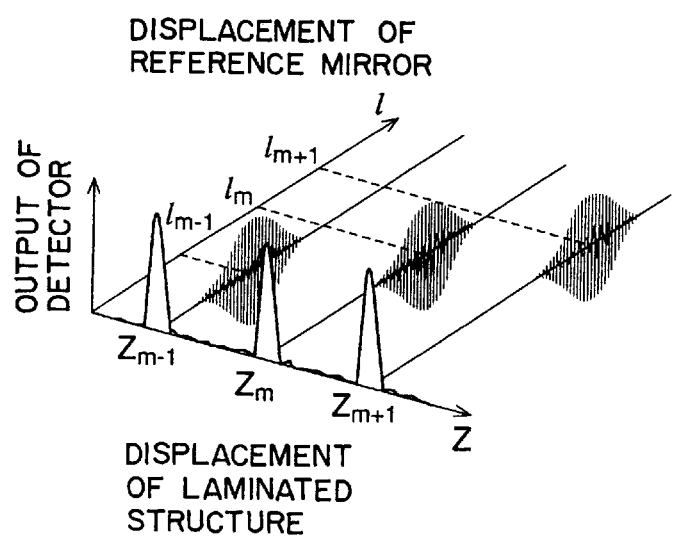
F I G. 2

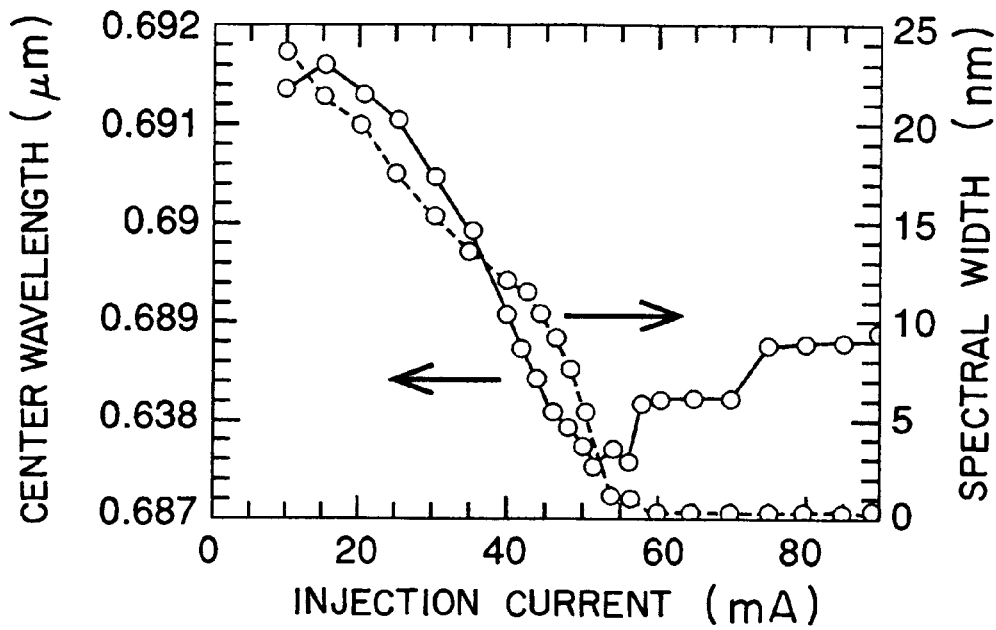
F I G. 5
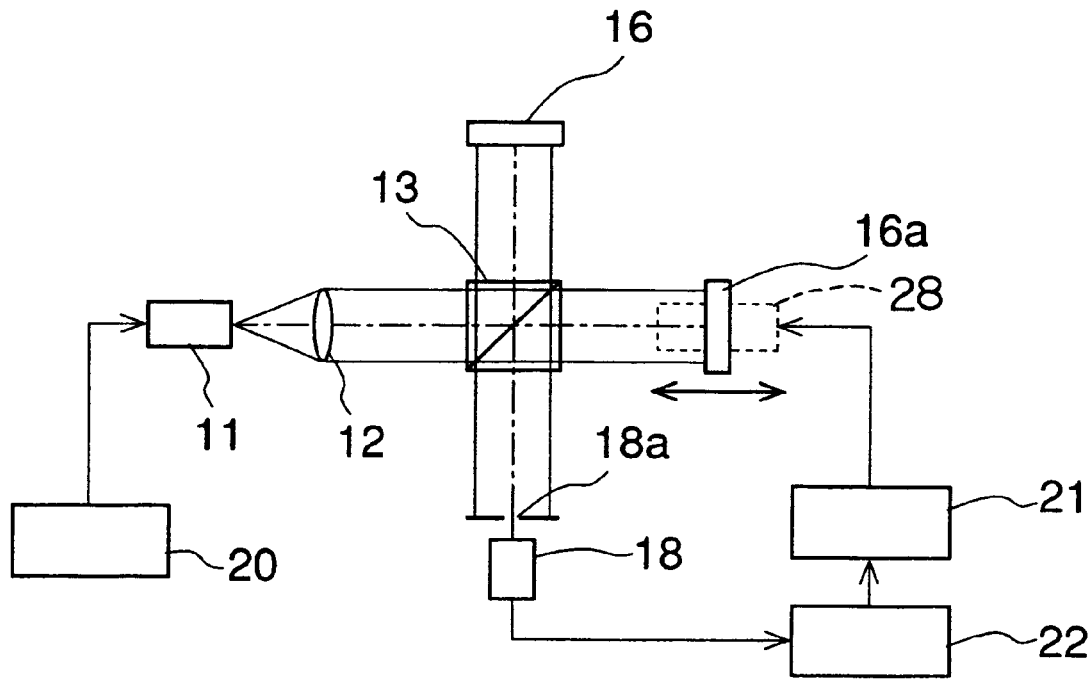
F I G. 6

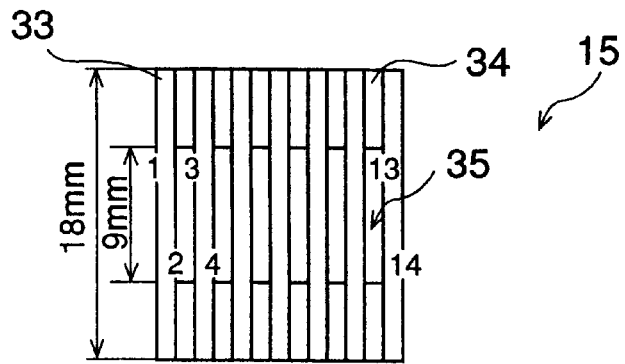
F I G. 12 A
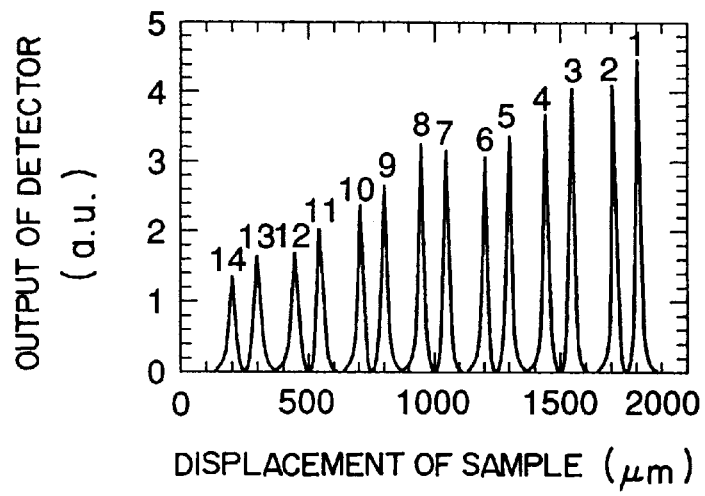
F I G. 12 B
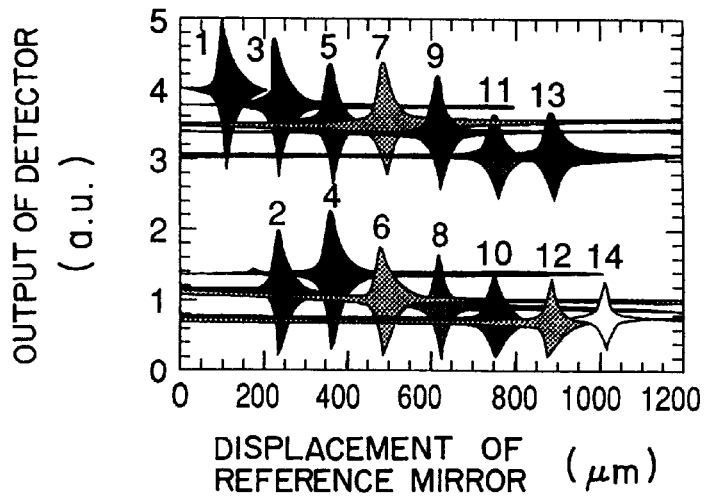
F I G. 12 C

METHOD OF MEASURING THICKNESS AND REFRACTIVE INDICES OF COMPONENT LAYERS OF LAMINATED STRUCTURE AND MEASURING APPARATUS FOR CARRYING OUT THE SAME

BACKGROUND OF THE INVENTION

1. Field of the Invention

The present invention relates to a method measuring the thicknesses and the refractive indices of component layers of a sample laminated structure, and a measuring apparatus for carrying out the same.

2. Description of the Related Art

A low-coherence interferometry is used for measuring the optical thickness of a transparent sample, such as a thin film or an optical glass. The low-coherence interferometry is carried out by an interferometer using white light or light emitted by a low-coherence light source, such as a light emitting diode. The low-coherence interferometry finds out the absolute position of a sample from the position of a reference mirror by using a fact that interference fringes appear only near a position where the difference between the two optical path lengths is zero. The low-coherence interferometry is applied to the absolute measurement of a block gage, the calibration of a base line and surface protilometry. Recently, active studies on a measuring method developed by extending the low-coherence interferometry have been reported in the fields of ophthalmology and biological science.

A known confocal laser microscope projects a laser beam on a sample in a spot, and forms an image of reflected light reflected by the sample or fluorescent light emitted by the sample on a point detector. The confocal laser microscope, as compared with conventional optical microscopes, is capable of forming an image of a high contrast and of forming a three-dimensional image with a high axial resolution, i.e., resolution along the optical axis. Therefore, the confocal laser microscope is used prevalently for measuring the morphology of a surface and observing biological specimens. The high axial resolution of the confocal laser microscope is effectively applicable to the measurement of optical thicknesses of component layers of a transparent laminated structure.

However, a value directly determined on the basis of the principle of the confocal laser microscope is an optical thickness and hence the refractive index of the corresponding layer must be determined by another method to convert the optical thickness into a corresponding geometrical thickness. Such a problem arises also in thickness measurement by the foregoing low-coherence interferometry. However, there has not been proposed any refractive index measuring method capable of measuring the respective indices of the component layers of a sample laminated structure without destroying the sample laminated structure.

SUMMARY OF THE INVENTION

The present invention has been made in view of the problem in the prior art and it is therefore an object of the present invention to provide a method of measuring the thicknesses and the refractive indices of component layer of a laminated structure and a measuring apparatus for carrying out the same.

According to a first aspect of the present invention, a measuring apparatus for measuring thicknesses and refractive indices of component layers of a laminated structure comprises a light source which projects a light beam on the laminated structure, a beam splitter disposed between the light source and the laminated structure, an objective disposed between the point light source and the laminated structure, a reference mirror disposed on a straight line intersecting a straight line connecting the point light source and the laminated structure and passing the beam splitter on one side of the beam splitter, and a detector disposed on the straight line on the other side of the beam splitter. The laminated structure and the reference mirror are movable, and a data processing means calculates the thickness and the refractive index of the mth layer of the laminated structure on the basis of a displacement of the laminated structure and that of the reference mirror between a condition where an interference signal reaches a maximum when one of the surfaces of the mth layer is at the first focal point of the objective, and a condition where an interference signal reaches a maximum when the other surface of the mth layer is at the second focal point of the objective indicated by confocal signals and interference signals provided by the detector.

According to a second aspect of the present invention, a method of measuring thicknesses and refractive indexes of component layers of a laminated structure by using a measuring apparatus comprising a light source which projects a light beam on the laminated structure, a beam splitter disposed between the light source and the laminated structure, an objective disposed between the light source and the laminated structure, a movable reference mirror disposed on a straight line intersecting a straight line connecting the light source and the laminated structure and passing the beam splitter on one side of the beam splitter, and a detector disposed on the straight line on the other side of the beam splitter comprises: projecting a light beam by the light source through the beam splitter and the objective on the laminated structure; moving the laminated structure and the reference mirror on the basis of a confocal signal provided by the detector upon the reception of a reflected light beam traveling from the laminated structure to the detector through the beam splitter and an interference signal provided by the detector upon the reception of the reflected light beam and a reference light beam traveling through the beam splitter and the reference mirror to the detector so that one of the surfaces of the mth layer of the laminated structure is positioned at a first focal point of the objective and the reference mirror is positioned at a first reference mirror position where the interference signal reaches a maximum; moving the laminated structure and the reference mirror on the basis of the confocal signal and the interference signal provided by the detector so that the other surface of the mth layer of the laminated structure is positioned at the focal point of the objective and the reference mirror is positioned at a second reference mirror position where the interference signal reaches a maximum; and determining the thickness and the refractive index of the mth layer of the laminated structure on the basis of the displacement of the laminated structure from the first focal point where one surface of the mth layer is at the focal point of the objective to the second focal point where the other surface of the mth layer is at the focal point of the objective, and the displacement of the reference mirror from the first reference mirror position to the second reference mirror position.

According to the present invention, the laminated structure and the reference mirror are moved from the first focal point and the first reference mirror position to the second focal point and the second reference mirror position, respectively, on the basis of the confocal signal provided by the detector upon the reception of the reflected light beam and the interference signal provided by the detector upon the reception of the reflected light beam and the reference light beam, and the thickness and the refractive index of the mth layer of the laminated structure are determined on the basis of the respective displacements of the laminated structure and the reference mirror.

BRIEF DESCRIPTION OF THE DRAWINGS

The above and other objects, features and advantages of the present invention will become more apparent from the following description taken in connection with the accompanying drawings, in which:

FIG. 1A is a diagrammatic view of a measuring apparatus in accordance with the present invention for measuring the thicknesses and the refractive indices of component layers of a laminated structure;

FIGS. 1B and 1C are diagrammatic views of assistance in explaining the position of a laminated structure relative to an objective included in the measuring apparatus of FIG. 1A;

FIG. 2 is a diagrammatic view of assistance in explaining a method of measuring the thicknesses and the refractive indices of a component layers of a laminated structure;

FIG. 5 is a graph showing the respective variations of the center wavelength and the spectral line width of light emitted by a laser diode with current supplied to it;

FIG. 6 is a diagrammatic view of a Michelson interferometer;

FIG. 12A is a typical view of another sample; and

FIGS. 12B and 12C are graphs showing the variation of the output signals of a detector when measuring the sample shown in FIG. 12A.

DESCRIPTION OF THE PREFERRED EMBODIMENTS

Figure 3:
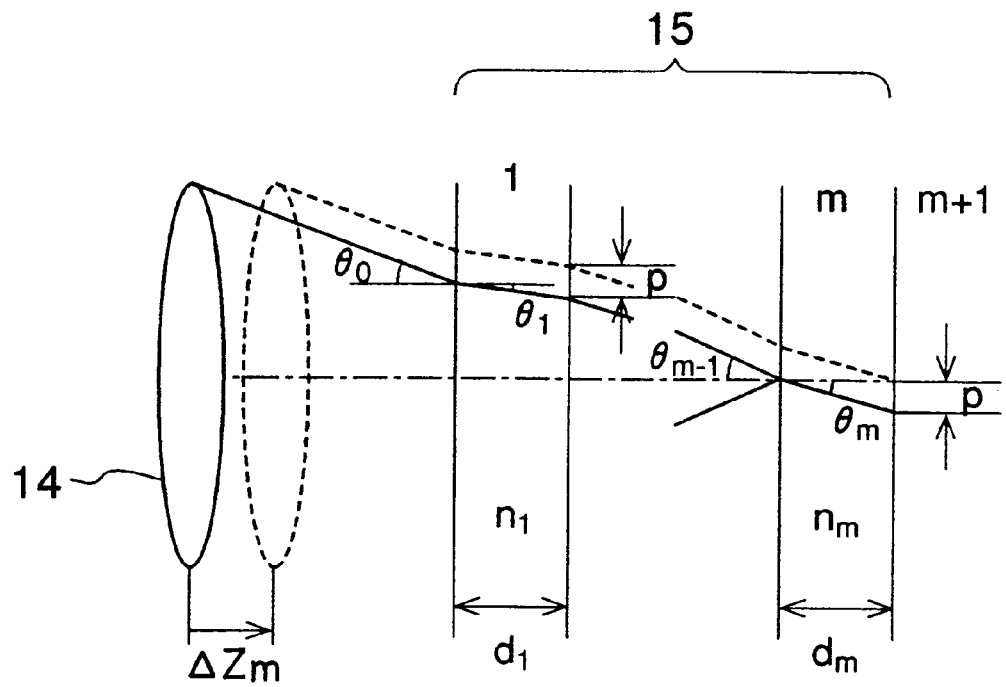
FIG. 3 is a diagrammatic view of assistance in explaining the change of a marginal ray governing position with the displacement of a sample relative to an objective.

A basic principle of the present invention will be described with reference to FIGS. 1 to 3 prior to the description of the preferred embodiments of the present invention.

Referring to FIGS. 1A to 1C, a measuring apparatus 10 for measuring thicknesses and refractive indices of component layers of a laminated structure comprises a point light source 11 (low-coherence light source) which projects a light beam through a pinhole 11a on a sample 15, i.e., a laminated structure, and collimator lens 12, a beam splitter 13 and an objective 14 arranged in that order between the point light source 11 and the sample 15. A reference mirror 16 is disposed on a straight line $L_2$ intersecting a straight line $L_1$ interconnecting the point light source 11 and the sample 15 on one side of the beam splitter 13. A condenser lens 17, and a detector 18 provided with a pinhole 18a are disposed on the straight line $L_2$ on the other side of the beam splitter 13. The optical system of the measuring apparatus 10 shown in FIG. 1A is a combination of a Michelson interferometer and a confocal system. The light beam emitted by the point light source 11 is focused on the sample 15 by the objective 14 disposed near the sample 15. The light beam reflected by the sample 15 is gathered by the condenser lens 17 on the pinhole 18a, and the light beam transmitted through the pinhole 18a is detected by the detector 18. The point light source 11, the objective 14 and the detector 18 constitute the confocal system. The measuring apparatus 10 using the point light source 11 which emits a light beam of a wide wavelength spectral width serves as a low-coherence interferometer.

Suppose that the sample 15 shown in FIG. 1A is a transparent laminated structure. The optical system functions as a confocal system when the reference mirror 16 is screened to block a reference optical path. In this state, the light beam emitted by the point light source 11 travels through the collimator lens 12, the beam splitter 13 and the objective 14 to the sample 15. The reflected light beam reflected by the sample 15 travels through the objective 14, the beam splitter 13 and the condenser lens 17 to the detector 18. Upon the reception of the reflected light beam, the detector provides a confocal signal. As the sample 15 is moved toward the objective 14, a peak appears in the output of the detector 18 upon the arrival of an interface between the adjacent component layers of the sample 15 at a focal point of the objective 14. As the sample 15 is moved further toward the objective 14, peaks appear successively in the output of the detector 18 as the interfaces between the adjacent component layers of the sample 15 arrive at a focal point of the objective 14 successively, as indicated by peaks on the Z-axis of the graph of FIG. 2. Thus, the arrival of each interface at the focal point of the objective 14 can be known from the peak in the output signal of the detector.

When the sample 15 is fixedly disposed with the mth interface, i.e., an interface between layers of (m−1)th and mth from the surface of the sample 15 facing the objective 14, positioned at the focal point of the objective 14 as shown in FIG. 1B and the reference mirror 16 is unscreened, the reflected light beam reflected by the sample 15 travels through the objective 14, the beam splitter 13 and the condenser lens 17 to the detector 18, and part of the light beam emitted by the point light source 11 travels, as a reference light beam, through the collimator lens 12, the beam splitter 13, the reference mirror 16 and the condenser lens 17 to the detector 18. Then, the detector 18 provides an interference signal on the basis of the reflected light beam and the reference light beam. In this state, the sample 15 is positioned at a first position.

The reference mirror 16 is then moved to a first reference mirror position where the reference light beam makes the amplitude of the interference signal increase to a maximum. In this state, the optical path difference between the two optical paths of the interferometer is zero.

Then, the sample 15 is advanced toward the objective 14 by a distance $\Delta Z_m$ to focus the light beam on the (m+1)th interface as shown in FIG. 1C. In this state, the (m+1)th interface is at the focal point of the objective 14. In this state, the sample 15 is positioned at a second position but the condition for equal optical path length is not met because the position of the reference mirror 16 is not changed. Therefore, the reference mirror 16 is moved by a distance $\Delta l_m$ to a second reference mirror position to reduce the optical path difference to zero.

A series of such operations enables the measurement of the optical thickness of the mth layer on two different principles; that is, the optical thickness of the mth layer is measured by both a method using a confocal system and a low-coherence interference method. Therefore, an optical path length, i.e., (refractive index)×(thickness), can be expressed by two expressions, and the refractive index and the thickness of the layer can be determined by solving the two expressions. A procedure for making those expressions will be described hereinafter.

Suppose that the focal point is moved from the mth interface to the (m+1)th interface by the confocal optical system as shown in FIG. 3, in which the objective 14 is shifted to simplify the procedure for making the expressions. When the (m+1)th interface is positioned at the focal point, all the intersection points of marginal rays and each interface are translated evenly away from the optical axis. From FIG. 3, $$\tan\theta_0 = \frac{p}{\Delta Z_m} \quad (1)$$

$$\tan\theta_m = \frac{p}{d_m} \quad (2)$$

where p is the displacement of the intersection point of the marginal rays and the interface, $\theta_0$ is the incident angle of the peripheral rays on the first layer, $\theta_m$ is the refractive angle at the mth interface, and $d_m$ is the geometrical thickness of the mth layer. The following expression is obtained by eliminating p from Expressions (1) and (2).

$$d_m \tan\theta_m = \Delta Z_m \tan\theta_0 \quad (3)$$

Since the marginal rays are refracted at each interface according to Snell's law, $$n_m \sin\theta_m = n_0 \sin\theta_0 = N.A. (m=1,2,\ldots m,\ldots) \quad (4)$$

where N.A. is the numerical aperture of the objective 14.

Conditions for establishing an equal optical path length state, i.e., a state in which the optical path length of two optical paths are equal to each other, by the low-coherence interference method will be considered. The conditions for the equal optical path length state become unsatisfied when the sample 15 is shifted. A displacement $\Delta l_m$ by which the reference mirror 16 needs to be shifted to satisfy the conditions for the equal optical path length state is the sum of a decrement $\Delta Z_m$ in the optical path in air resulting from the movement of the sample 15 toward the objective 14, and an increment $n_m \times d_m$ in the optical path length resulting from the passage of the light beam through the mth layer. Therefore, $$\Delta l_m = n_m d_m - \Delta Z_m \quad (5)$$

The geometrical thickness $d_m$ and the refractive index $n_m$ of the mth layer are determined by solving simultaneous equations (3) to (5).

$$n_m^2 = \frac{1}{2}\left[N.A.^2 + \sqrt{N.A.^4 + 4(1-N.A.^2)\left(1 + \frac{\Delta l_m}{\Delta Z_m}\right)^2}\right] \quad (6)$$

$$d_m = \frac{\Delta l_m + \Delta Z_m}{n_m} \quad (7)$$

This procedure is repeated for the successive layers to determine the respective geometrical thicknesses and the respective refractive indices of the layers.

Example

A preferred example of the present invention will be described hereinafter.

Characteristics of Laser Diode

A laser diode (TOLD-9150, threshold current: 52 mA, available from Toshiba) was employed as the point light source 11 and the laser diode was driven by a current below the threshold current to use the laser diode as a light emitting diode. A light beam emitted by the point light source 11 has a wide spectrum and hence the point light source 11 functions as a low-coherence light source Since the point light source 11 has a minute light emitting region the point light source 11 need not be provided With the pinhole 11a. The characteristics of the point light source 11 will be explained in terms of measured spectrum and measured coherence length.

Measurement of Spectrum

Figure 4:
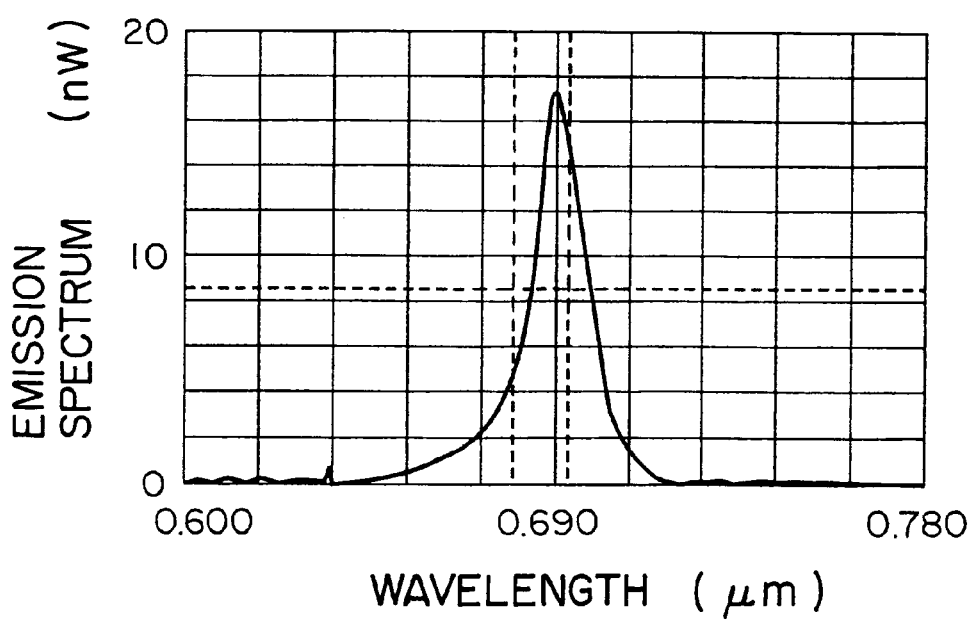
FIG. 4 is diagram showing the spectrum of light emitted by a point light source.

The dependence of the spectrum of the light beam emitted by the point light source 11 on current supplied to the point light source 11 was examined by using an optical spectrum analyzer (Advantest Q8344A). FIG. 4 shows the spectrum of the light beam emitted by the point light source when a current of 30 mA was supplied to the point light source 11, in which center wavelength is 690.5 nm and the full width at half maximum of the spectrum is 15.3 nm. The emission power was 50 $\mu$W. FIG. 5 shows the current dependence of the center wavelength and the full width at half maximum of the spectrum. It is known from FIG. 5 that the center wavelength decreases with the increase of the current, laser oscillation occurs when the current exceeds the threshold current, and the center wavelength resume to increase stepwise (mode hop) with the increase of the current. It is also known from FIG. 5 that the width of the spectrum decreases gradually with the increase of the current, decreases sharply with the variation of the current around the threshold current, and remains substantially constant after the start of laser oscillation.

Measurement of Coherence Length

Coherence length was measured by a Michelson interferometer shown in FIG. 6, in which a plane mirror 16a was moved along an optical axis. A point light source 11 is driven by a driving unit 20, the plane mirror 16a is mounted on a linear stage 28 driven by a stepping motor. The operation of the driving unit 20 and the linear stage 28 is controlled by a controller 21. A detector 18 is connected to a personal computer 22 controlling the controller 21.

Figure 7A:
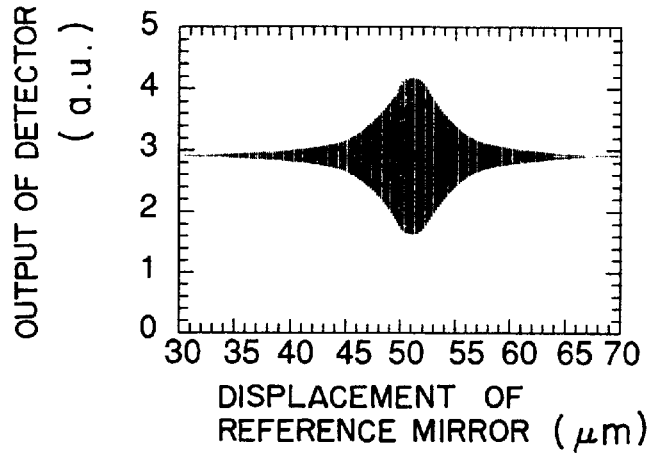
FIG. 7A is a graph showing the output of the detector in the Michelson interferometer of FIG. 6.
Figure 7B:
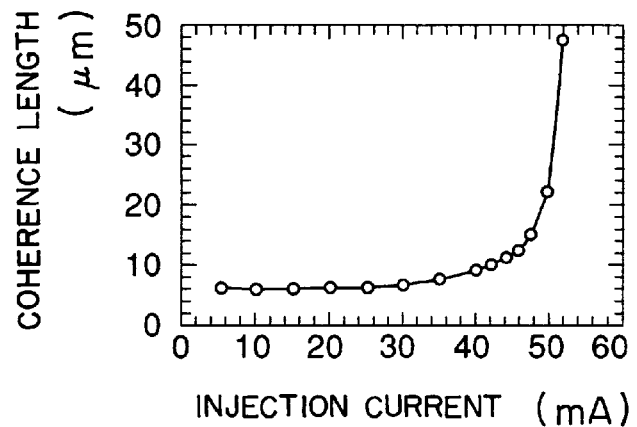
FIG. 7B is a graph showing the coherence length of the laser output in Michelson interferometer of FIG. 6.

FIG. 7A shows an interferogram when a current of 30 mA was supplied to the point light source 11. The plane mirror 16a was moved stepwise in steps of 0.1 pm. The full width at a half maximum, i.e., the coherence length, was 6.9 $\mu$m. The current was varied in a current range below the threshold current for the same measurement to examine the current dependence of the coherence length. The results are shown in FIG. 7B. It is known from FIG. 7B that the coherence length varies scarcely when the current is below 35 mA, and increases sharply with the current after the current in creases beyond the threshold current. In the following experiments, a driving current of 30 mA was used taking into consideration the output power of the laser diode, i.e., the point light source, and the coherence length.

Simultaneous Measurement of Thickness and Refractive Index

Experimental Optical System

Figure 8:
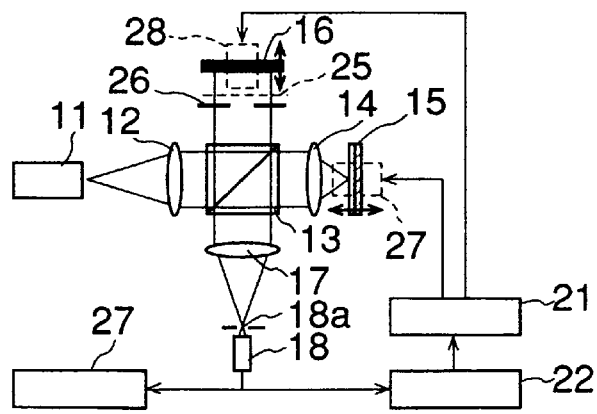
FIG. 8 is a diagrammatic view of a measuring apparatus in a preferred embodiment according to the present invention for measuring the thicknesses and the refractive indices of component layers of a laminated structure.

Referring to FIG. 8, a collimator lens 12 collimates rays of a light beam emitted by a point light source, i.e., a laser diode. The collimated light beam travels through a beam splitter 13 is focused on a sample 15 by a objective 14 (MD Plan, magnification: ×10, Effective N.A.: 0.21, W.D.: 7 mm, Olympus). The light beam reflected by the beam splitter 13 is used as a reference light beam. In a detection system, the reflected light beam is gathered on a pinhole 18a of 10 μm in diameter by a condenser lens 17, and the light beam traveled through the pinhole 18a is detected by a detector 18, i.e., a photomultiplier tube (Optical Sensor Module H5783-01, Hamamatsu Photonics). The output signal of the detector 18 is monitored by an oscilloscope 27 and is given through an AD board, not shown, to a personal computer 22. The sample 15 and a reference mirror 16 are mounted on linear stages 27 and 28 driven by stepping motors, respectively. The linear stages 27 and 28 can be moved in steps of 1 μm and 0.1 μm, respectively, by giving pulse signal through a PIO board, not shown, by the personal computer to a controller 21. A shutter 25 and a variable aperture 26 are disposed on the optical path of the reference light beam. The intensity of the reference light beam is regulated by regulating the diameter of the reference light beam by the variable aperture 26.

The laser diode serving as the point light source 11 is made to perform laser oscillation when adjusting the optical system, and a current not higher than the threshold current is supplied to the laser diode to use the laser diode as a light emitting diode for measurement Experiments First, the sample 15 is disposed close to the objective 14, and then the sample 15 is moved away from the objective 14 to prevent the sample 15 from coming into contact with the objective 14. In this state, the reference light beam is intercepted by the closed shutter 25. The position of a peak is determined by subjecting a confocal signal to smoothing differentiation. The position of the sample 15 is adjusted on the basis of the data representing the position of the peak so that a surface thereof nearest to the objective 14 is positioned at the focal point of the objective 14. Subsequently, the shutter 25 is opened the gain of the photomultiplier of the detector 18 and the reference mirror 16 is moved away from the beam splitter 13 for a scanning operation. After the completion of the scanning operation, the sample 15 and the reference mirror 16 are returned to their initial positions, respectively, the sample 15 is moved again on the basis of the data representing the position of the peak so that the next interface is positioned at the focal point, and then the reference mirror 16 is moved again for a scanning operation. The foregoing procedure is repeated for all the interfaces of the sample 15. Although the return of the sample 15 and the reference mirror 16 to their initial positions takes an additional time, the influence of backlashes in the linear stages 27 and 28 can be reduced. The detection of the position of the peak of the confocal signal for the analysis of signals was carried out in an on-line mode, and the interferogram was analyzed after transferring the data to a work station.

Axial Response of the Confocal System and Interferogram

Figure 9A:
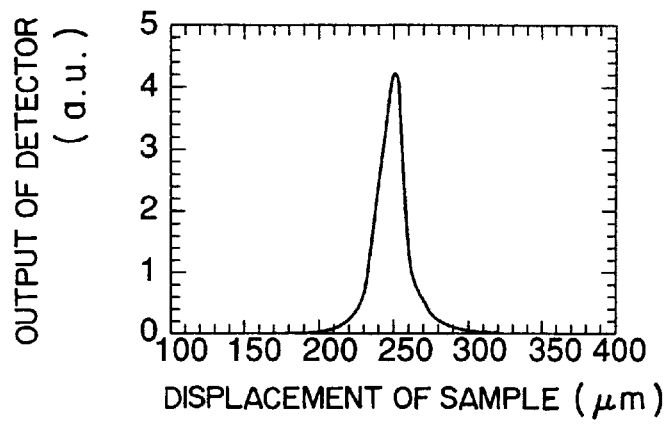
FIG. 9A is a graph showing the variation of the output of a detector with the position of a sample.
Figure 9B:
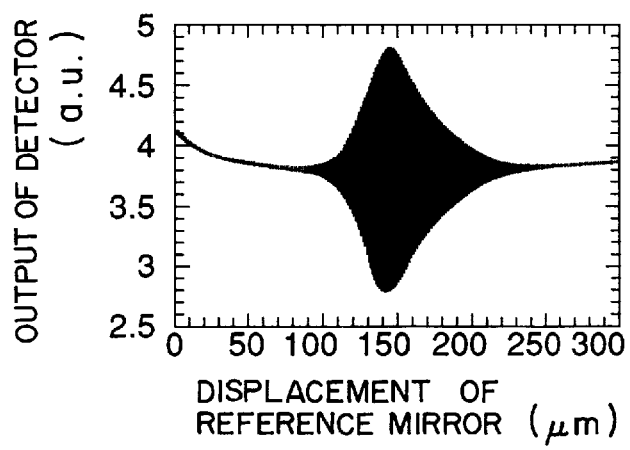
FIG. 9B is a graph showing the variation of the output of a detector with the position of a reference mirror.

The optical plane mirror 16a (FIG. 6) was used for measurement to confirm if the optical system is functioning as both the confocal system and the low-coherence interferometer. FIG. 9A shows the axial response of the confocal system when the optical plane mirror 16a, i.e., the sample, was moved. An interferogram as shown in FIG. 9B was obtained by fixedly holding the optical plane mirror 16a at a position corresponding to the peak in the output signal of the detector 18, and moving the reference mirror 16. Full widths at half maximum determined from those results were 20 μm and 46 μm. It is known from FIG. 9B that the interferogram, as compared with the interferogram shown in FIG. 7A obtained by measurement in a free space, is asymmetrical, and the full width at half maximum is about seven times. Formation of such an asymmetrical interferogram and such increase in the full width at half maximum are considered to be attributable to (a) the spherical aberration caused by the objective 14, and (b) dispersion caused by the objective lens 14. Substantially the same results as those shown in FIG. 9B were obtained through measurement using a diaphragm disposed just behind the objective 14 to narrow the light beam. Therefore, it is considered that the effect of dispersion caused by the objective 14 is more dominant than that of the spherical aberration caused by the objective 14. The effect of dispersion could be canceled by replacing the reference mirror 16 with a cat's eye consisting of a lens identical with the objective disposed near the sample 15 and a plane mirror.

Results of Experiments and Examination of the Results

Samples including a parallel plane base plate, a three-layer liquid crystal evaluation glass cell (hereinafter, referred to as "liquid crystal cell") and a thirteen-layer sample fabricated by stacking cover glasses were subjected to measurement. Measurements of the three-layer liquid crystal cell and the thirteen-layer sample are given below by way of example.

Figure 10:
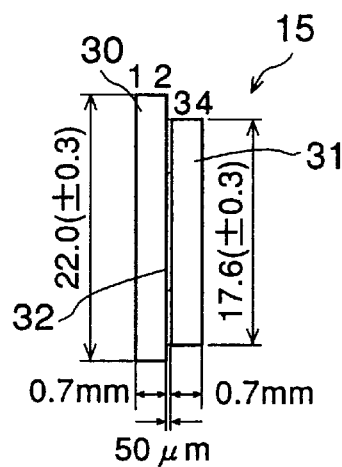
FIG. 10 is a typical view of a sample.
Figure 11A:
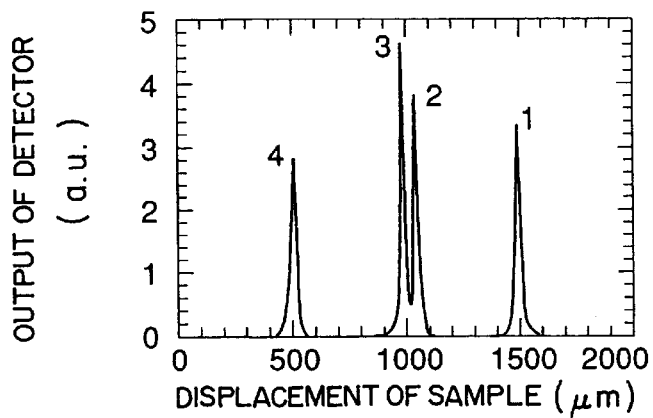
FIGS. 11A to 11D are output signals of a detector when measuring the sample shown in FIG. 10.
Figure 11B:
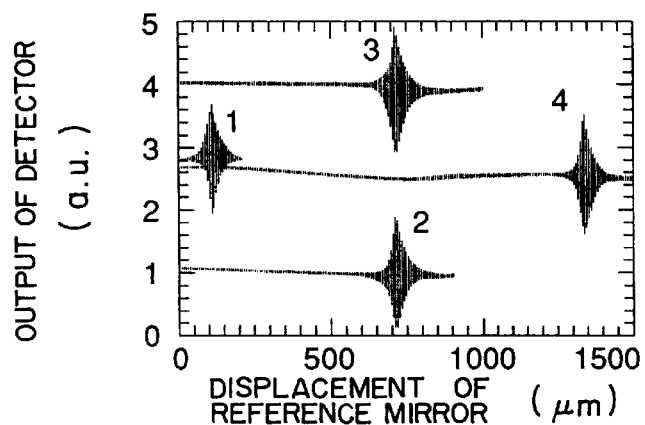
Figure 11C:
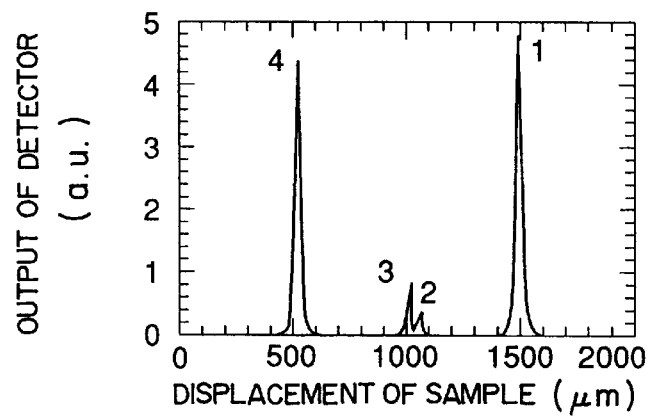
Figure 11D:
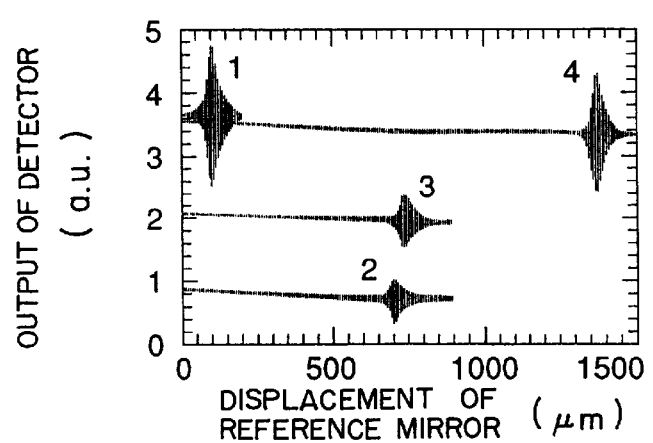

Referring to FIG. 10 a sample liquid crystal cell 15 (EHC K.K.) was fabricated by combining two glass plates 30 and 31 of 0.7 μm in thickness and 1.51 in refractive index so that a 50 μm thick space 32 was formed between the glass plates 30 and 31. The space 32 was kept void for a condition A, and the space 32 was filled up with pure water for a condition B. FIGS. 11A to 11D show measured results. FIGS. 11A and 11B show the results of measurement under the condition A, and FIGS. 11C and 11D show the results of measurement under the condition B. FIGS. 11A and 11C show data representing the response of the confocal system, in which peaks 1, 2, 3 and 4 are the output signals of the detector when the light beam was focused on the interfaces indicated by the same numerals, respectively. FIGS. 11B and 11D show interferograms, in which numerals indicating the interferograms corresponds to positions of the sample liquid crystal at which the peaks indicated by the same numerals shown in FIGS. 11A and 11C appear, respectively. FIGS. 11A and 11B shows the signals after adjusting the bias properly to facilitate understanding. The values of the peaks 2 and 3 in FIG. 11C are small as compared with those of the corresponding peaks 2 and 3 in FIG. 11A because the refractive index of pure water is closer to that of glass than that of air and hence the reflectivity of the interface is low. Whereas the localized positions of the interferograms for the condition A are not changed, those of the interferograms for the condition B are displaced, which can be reasoned from a fact that the distance between the objective and the sample is reduced by the thickness of the space 32 and the optical path length does not change when the sample is moved to change the focal position from the interface in front of the space 32 to the interface behind the space 32, if the space 32 is filled with air.

FIG. 12A shows a thirteen-layer sample 15 fabricated for the experiment by alternately stacking cover glasses 33 and 34 (thickness: 0.145±0.015 mm, refractive index: 1.523 (λ=588 nm), Matsunami Garasu Kogyo) and air space in a thirteen-layer structure. FIGS. 12B and 12C shown measured confocal signals and interferograms, respectively. In FIG. 12B, numerals indicating peaks corresponds to those indicating interfaces in FIG. 12A. The interferograms shown in FIG. 12C are produced after adjusting the bias. In FIG. 12B, the peaks indicated by greater numerals have smaller values because the quantity of light absorbed by the layers and the quantity of light reflected by the interfaces increases with depth from the surface of the sample 15 facing the objective 14 and hence the quantity of light reflected by the interface and falling on the detector 18 decreases with the depth of the interface from the surface of the sample 15 facing the objective 14. The interferograms relating to the deeper layers are distorted by color dispersion caused by the forward layers. The localization of the interferogram relating to the interfaces of the air layers do not change for the same reasons as those for the liquid crystal cell.

Table 1 shows the geometrical thicknesses and the refractive indices of the samples 15 calculated by using the data about the intervals between the peaks and the intervals between the localized interference fringes, and Expressions (6) and (7). Shown also in Table 1 are data about the other samples 15, thicknesses measured by a micrometer and nominal values shown in catalogs. With the samples 15 of 1 mm or above in thickness, those data coincide with each other with an error of 1% or below. Relative accuracy deteriorates when the thickness of the sample 15 decreases, which is supposed to occur because errors in the estimation of the position for equal optical path length are most effective in introducing errors into the final thickness and the refractive index.

TABLE 1

| Samples | Thickness ($\mu$m) | Refractive index |
| --- | --- | --- |
| Parallel plane plate (BK7) | 1084(1093)[b] | 1.513(1.514)[c] |
| Parallel plane plate (Fused Silica) | 1028(1020)[b] | 1.457(1.455)[c] |
| LC cell 1-2 (Glass)[a] | 701(717)[b] | 1.516(1.510 ± 0.015)[c] |
| 2-3 (Air)[a] | 54(50)[c] | 1.002(1.000)[c] |
| 3-4 (Glass)[a] | 728(717)[b] | 1.511(1.510 ± 0.015)[c] |
| LC cell 1-2 (Glass)[a] | 701(717)[b] | 1.517(1.510 ± 0.015)[c] |
| 2-3 (Water)[a] | 58(50)[c] | 1.345(1.510 ± 0.015)[c] |
| 3-4 (Glass)[a] | 724(717)[b] | 1.514(1.510 ± 0.015)[c] |
| Thirteen-layer sample | | |
| Glass 1-2, 3-4, 5-6 7-8, 9-10, 11-12 13-14 | 148, 149, 148, 150, 151, 151 | 1.537, 1.505, 1.502 1.537, 1.548, 1.525 1.506(1.523)[c)d] |
| Air 2-3, 4-5, 6-7, 8-9 10-11, 11-12 | 160, 149, 156 153, 162, 150 | 0.997, 1.009, 1.009, 0.987, 0.997, 1.007 (1.000)[c] |

[a] LC cell 1-2 corresponds to the peaks 1 and 2 in FIG. 2.
[b] Values measured by a micrometer
[c] Nominal values provided in catalogs
[d] $\lambda$ = 588 nm The present invention could measure accurately the thicknesses and refractive indices of the component layers of the samples 15 of laminated structures in which the opposite surfaces of each component layer are not exactly parallel to each other and each component layer has nonuniform thickness, such as an onion.

The component layers of the sample 15 may be of a material other than glass, such as a synthetic resin or the like, provided that the component layers are transparent to light of wavelength in the wavelength range of the light emitted by the point light source 11. If a laser diode which emits light of a wavelength in the near-infrared wavelength range is employed as the point light source 11, the present invention is applicable to the measurement of the thicknesses and the refractive indices of the component layers of semiconductor structures.

As is apparent from the foregoing description, according to the present invention, the sample and the reference mirror are moved from a first confocal position and a first reference mirror position for a first surface of the mth layer of the sample to a second confocal position and a second reference mirror position for a second surface of the mth layer, respectively. The thickness and the refractive index of the mth layer are determined on the basis of the respective displacements of the sample and the reference mirror. Thus, the thickness and the refractive index of the mth layer of a laminated structure can surely and easily be determined.

Although the invention has been described in its preferred form with a certain degree of particularity, obviously many changes and variations are possible therein. It is therefore to be understood that the present invention may be practiced otherwise than as specifically described herein without departing from the scope and spirit thereof.

What is claimed is:

1. A measuring apparatus for measuring thicknesses and refractive indices of component layers of a laminated structure, said measuring apparatus comprising:

a light source which projects a light beam on the laminated structure;

a beam splitter disposed between the light source and the laminated structure;

an objective disposed between the beam splitter and the laminated structure;

a reference mirror disposed on a straight line intersecting a straight line connecting the light source and the laminated structure and passing the beam splitter, on one side of the beam splitter;

a detector disposed on the straight line on the other side of the beam splitter;

a first stage for moving the laminated structure along the optical axis of the objective, and, a second stage for moving the reference mirror along an optical axis perpendicular to the mirror, and wherein a data processing means calculates the thickness and the refractive index of an mth layer of the laminated structure on the basis of a displacement of the laminated structure and the reference mirror to respective positions corresponding to a first condition where a first surface of the mth layer is at a focal point of the objective and an interference signal provided by the detector reaches a maximum, and a second condition where a second surface of the mth layer is at the focal point of the objective and an interference signal provided by the detector reaches a maximum.

2. The measuring apparatus according to claim 1, wherein the data processing means calculates the thickness $d_m$ and the refractive index $n_m$ of the mth layer by using expressions:

$$n_m^2 = \frac{1}{2}\left[N.A.^2 + \sqrt{N.A.^4 + 4(1 - N.A.^2)\left(1 + \frac{\Delta l_m}{\Delta Z_m}\right)^2}\right]$$

$$d_m = \frac{\Delta l_m + \Delta Z_m}{n_m}$$

where N.A. is the numerical aperture of the objective, $\Delta l_m$ is the displacement of the reference mirror, and $\Delta Z_m$ is the displacement of the laminated structure.

3. The measuring apparatus according to claim 1, wherein the opposite surfaces of at least one of the plurality of layers of the laminated structure are not parallel to each other, and the thickness of the same layer varies over the entire region of the laminated structure.

4. A method of measuring thicknesses and refractive indices of component layers of a laminated structure by using a measuring apparatus comprising: a light source which projects a light beam on the laminated structure, a beam splitter disposed between the light source and the laminated structure, an objective disposed between the beam splitter and the laminated structure, a reference mirror disposed on a straight line intersecting a straight line connecting the light source and the laminated structure and passing the beam splitter, on one side of the beam splitter, and a detector disposed on the straight line on the other side of the beam splitter, wherein the laminated structure is movable along the optical axis of the objective, the reference mirror is movable along its optical axis; said method comprising the steps of:

projecting a light beam by the light source through the beam splitter and the objective on the laminated structure;

moving the laminated structure and the reference mirror on the basis of a confocal signal provided by the detector upon the reception of the reflected light beam traveled from the laminated structure to the detector through the beam splitter and an interference signal provided by the detector upon the reception of the reflected light beam and a reference light beam traveling through the beam splitter and reference mirror to the detector so that one of the surfaces of the mth layer of the laminated structure is positioned at a focal point of the objective and the reference mirror is positioned at a first reference mirror position where the reference mirror reflects the interference signal reaches a maximum;

moving the laminated structure and the reference mirror on the basis of the confocal signal and the interference signal provided by the detector so that the other surface of the mth layer of the laminated structure is positioned at the focal point of the objective and the reference mirror is positioned at a second reference mirror position where the interference signal reaches a maximum; and determining the thickness and the refractive index of the mth layer of the laminated structure on the basis of a displacement of the laminated structure from a first position where one surface of the mth layer is at the focal point of the objective to a second position where the other surface of the mth layer is at the focal point of the objective, and a displacement of the reference mirror from the first reference mirror position to the second reference mirror position.

5. The method according to claim 4, wherein the process of determining the thickness and the refractive index of the mth layer determines the same by using expressions:

$$n_m^2 = \frac{1}{2}\left[N.A.^2 + \sqrt{N.A.^4 + 4(1 - N.A.^2)\left(1 + \frac{\Delta l_m}{\Delta Z_m}\right)^2}\right]$$

$$d_m = \frac{\Delta l_m + \Delta Z_m}{n_m}$$

where N.A. is the numerical aperture of the objective, $\Delta l_m$ is the displacement of the reference mirror, and $\Delta Z_m$ is the displacement of the laminated structure.

6. The method according to claim 4, wherein the laminated structure has a plurality of layers, the opposite surfaces of at least one of the plurality of layers of the laminated structure are not parallel to each other, and the thickness of the same layer varies over the entire region of the laminated structure.

* * * * *